United States Patent [19]
Vo-Dinh

[11] Patent Number: 5,400,136
[45] Date of Patent: Mar. 21, 1995

[54] SURFACE-ENHANCED RAMAN SCATTERING (SERS) DOSIMETER AND PROBE

[75] Inventor: Tuan Vo-Dinh, Knoxville, Tenn.

[73] Assignee: Martin Marietta Energy Systems, Inc., Oak Ridge, Tenn.

[21] Appl. No.: 821,684

[22] Filed: Jan. 16, 1992

[51] Int. Cl.$^6$ .................. G01J 3/44; G01N 21/65
[52] U.S. Cl. ............................................ 356/301
[58] Field of Search ................................. 356/301

[56] References Cited

U.S. PATENT DOCUMENTS

| | | | |
|---|---|---|---|
| 4,674,878 | 6/1987 | Vo-Dinh | 356/301 |
| 4,680,165 | 4/1992 | Vo-Dinh | 422/88 |
| 4,781,458 | 11/1988 | Angel et al. | 356/301 |
| 5,255,067 | 10/1993 | Carrabba et al. | 356/301 |

*Primary Examiner*—F. L. Evans
*Attorney, Agent, or Firm*—Andrew S. Neely; Joseph A. Marasco; Harold W. Adams

[57] ABSTRACT

A dosimeter and probe for measuring exposure to chemical and biological compounds is disclosed. The dosimeter or probe includes a collector which may be analyzed by surface-enhanced Raman spectroscopy. The collector comprises a surface-enhanced Raman scattering-active material having a coating applied thereto to improve the adsorption properties of the collector. The collector may also be used in automated sequential devises, in probe array devices.

19 Claims, 4 Drawing Sheets

SURFACE-ENHANCED RAMAN SCATTERING (SERS) DOSIMETER AND PROBE

The United States Government has rights in this invention pursuant to contract No. DE-AC05-84OR21400 awarded by the United States Department of Energy.

TECHNICAL FIELD

The present invention relates to a collector useful for surface-enhanced Raman spectroscopy. More particularly, the present invention relates to a dosimeter or probe for measuring exposure to chemical or biological compounds which utilizes a collector which may be analyzed by surface-enhanced Raman scattering (SERS) detection method.

Background of the Invention

A number of optical spectroscopic techniques have been developed to characterize solid-gas (vacuum), solid-liquid (electrolyte) and solid-solid interfaces. In particular, the chemical identity of surface-adsorbed molecular species can be determined with specificity using surface analysis spectroscopy (SAS), such as infrared transmission spectroscopy and electron energy loss spectroscopy, instead of surface electronic absorption spectroscopy or photoacoustic spectroscopy. For example, SAS techniques can be used in the analysis of molecules sorbed at the surface of an electrode within a working electrochemical cell.

Among the SAS methods, surface-enhanced Raman spectrometry has recently received considerable attention. Enhancements by factors of $10^3$ to $10^8$ can be realized in the surface enhanced Raman scattering (SERS) intensity for adsorbates on or near special rough metal surfaces. This phenomenon has been verified for adsorbates at silver, copper, and gold metal surfaces under both solution and vacuum conditions. See, e.g., Albrecht & Creighton, 99 J. AM. Chem. SOC. 5215 (1977). These spectacular enhancement factors help overcome the normally low sensitivity of Raman spectroscopy which had often necessitated the use of powerful, costly laser sources for excitation. Because of these enhancement factors, it has been desired to utilize SERS media to monitor exposure to toxic substances.

It has been experienced, however, that because of the requirement for a metal surface for the SERS effect to be effective, most SERS media have limited usefulness in environments where the compounds do not adsorb easily onto the metal surface. Therefore, it has not been possible to utilize SERS media to monitor exposure to chemical compounds, such as many toxic organics, or biological species, such as bacteria or viruses, which do not adsorb easily onto a metal surface.

Therefore, a need exists for a SERS media having improved sorptivity and which may be utilized as a collector to monitor exposure to chemical and biological compounds which are not easily adsorbed onto conventional SERS media.

SUMMARY OF THE INVENTION

The present invention fills the above need by providing a dosimeter or probe which utilizes a collector useful for surface-enhanced Raman spectroscopy. The collector comprises a surface-enhanced Raman scattering (SERS)-active material having a coating thereon to alter the adsorption properties of the collector, as compared to the active material alone.

Generally described, the present invention provides a collector for a dosimeter or probe, the collector comprising a SERS-active material and a coating applied to the SERS-active material having different sorptive properties for the predetermined materials than the SERS-active material, the coating being operable in the presence of the predetermined materials to sorb and thereby position the predetermined materials in the vicinity of the SERS-active material and thereby alter the SERS characteristics of the collector.

Another aspect of the present invention provides a dosimeter or probe for collection of chemical components or biological species for analysis by surface-enhanced Raman spectroscopy. The dosimeter comprises a diffusion chamber secured to and extending outwardly from a base to define an outer end of the chamber and an inner end of the chamber adjacent to the base, and a collector within the chamber. The collector comprises a SERS-active material having a coating applied to the SERS-active material having greater sorptive properties for the predetermined materials than the SERS-active material, the coating being operable in the presence of the predetermined materials to sorb and thereby position the predetermined materials in the vicinity of the SERS-active material and thereby alter the SERS characteristics of the collector.

Thus, it is an object of the present invention to provide an improved dosimeter and probe.

It is another object of the present invention to provide a collector which uses the SERS-active material as a sorbent agent and a Raman inducer.

It is also an object of the present invention to provide a dosimeter and probe useful for surface-enhanced Raman spectroscopy.

It is yet another object of the present invention to provide an improved collector for use in a dosimeter or probe.

A still further object of the present invention is to provide a coating composition which alters the adsorptivity of a collector as compared to the SERS-active material alone.

Other objects, features, and advantages of the present invention will become apparent upon reading the following specification, when taken in conjunction with the drawings and the appended claims.

DETAILED DESCRIPTION OF AN ILLUSTRATED EMBODIMENT

Figure 1:
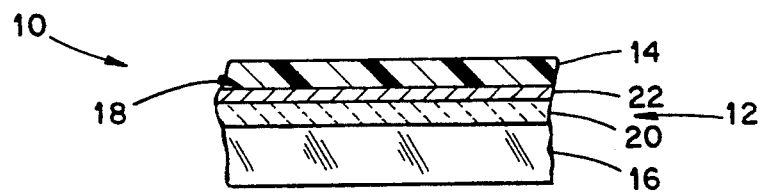
FIG. 1 is a cross-sectional end view of a collector made in accordance with the present invention.

Referring now to the drawings, in which the numerals refer to like parts throughout the several views, FIG. 1 shows a collector 10 made from a SERS-active material 12 having a coating 14 applied thereto to alter the sorptive properties of the collector 10 and thereby render the active material 12 more suitable for surface-enhanced Raman spectroscopy.

The SERS-active material 12 (hereinafter "SERS-active") includes a support base 16, such as a glass slide, and a roughened metal surface 18 having a degree of roughness sufficient to induce the SERS effect described above. The roughened surface 18 is preferably formed by applying a microparticle or microstructure layer 20 to the upper surface of the support base 16 and then depositing a metal layer 22 onto the microstructure layer 20. The roughened surface 18 may be formed using conventional techniques, such as described in U.S. Pat. No. 4,674,878, incorporated herein by reference.

For the SERS-active material 14 to be effective for measuring the concentration of a chemical or biological compound in a sampled environment, the monitored compound or compounds must be in the vicinity of the roughened surface 18. The coating 14 is applied to the roughened surface to sorb monitored compounds which are not easily adsorbed by the roughened surface and which are capable of either penetrating into the coating or being attached onto the coating. The monitored compounds thereby are "adsorbed" and become positioned in the vicinity of the roughened surface and exhibit the SERS effect. Thus, in essence, the coating serves to "alter" the adsorptivity of the roughened surface. The coating 14 may be an organic or inorganic sorbent material and is preferably an organic sorbent polymer coating, such as polymethyl-methacrylate (PMMA). Selection of the polymer is based on the sorbtivity of the polymer for the compound or compounds to be monitored. Selection criteria for coatings may be based upon the desired physical (e.g., size selectivity, permeability), chemical (e.g. polarity, chemical selectivity), electrical, magnetic, nuclear radiation-hardening and biological properties of the coating materials. Additionally, carbon compounds, such as activated charcoal or buckminster fullerene C-60, are contemplated for use as coatings in the present invention. Examples of other coating materials include those shown below:

Carnauba Wax
Ethyl cellulose
Ethylene maleic anhydride copolymer
Methyl vinyl ether
Octadecyl vinyl ether
Phenoxy resin
Poly 2-ethylhexyl methacrylate
Poly (Caprolactone)
Poly (Caprolactone) triol
Poly-1-butadiene
Poly-n-butyl acrylate
Poly-p-vinyl phenol
Polybutadiene oxide
Polybutadiene hydroxy terminated
Polybutadiene-methylacrylated
Polycutadiene acrylonitrile
Polydecyl acetate
Polyethyl acrylate
Polyethylene
Polyethylene glycol methyl ether
Polyhexyl methacrylate
Poly 1 butene
Polymethacrylate
Polystyrene
Polyvinyl butyryl
Polyvinyl carbazole
Polyvinyl chloride
Polyvinyl isobutyl ether
Polyvinyl methyl ether
Polyvinyl stearate
Vinyl alcohol/vinyl/acetate copolymer For example, a collector useful to monitor compounds, such as terephthalic acid, was produced as shown in Example 1.

EXAMPLE 1

Glass slides were cut into small squares (1 cm × 1 cm) that served as the support bases. These glass slides were then cleaned with nitric acid, distilled water, and ethnology and dried using a stream of dried air. Alumina microparticles were used to form a microstructured surface. Drops of an aqueous suspension of alumina (type 0.1 CR) were delivered on the glass slide, which was then spun at 2000 rpm for 20 seconds using a conventional spin-coating device to uniformly spread the alumina on the surface of the glass. Silver was then thermally evaporated onto the alumina-coated glass strips under vacuum ($\sim 2 \times 10^{-6}$ torr) to form the metal layer.

Polymethyl methacrylate (PMMA) was used to coat freshly prepared alumina SERS substrates as follows. Various solutions of PMMA were prepared from chlorobenzene. A 20-$\mu$l aliquot of the PMMA solution was placed on the silver-coated side of the alumina substrate and was spread evenly on the surface the substrate. The substrate was then spun at 6000 rpm for 20 seconds to produce a thin coating of PMMA film. Next, the film-coated substrates were placed under an infrared lamp to dry for 15 minutes before use.

Figure 2:
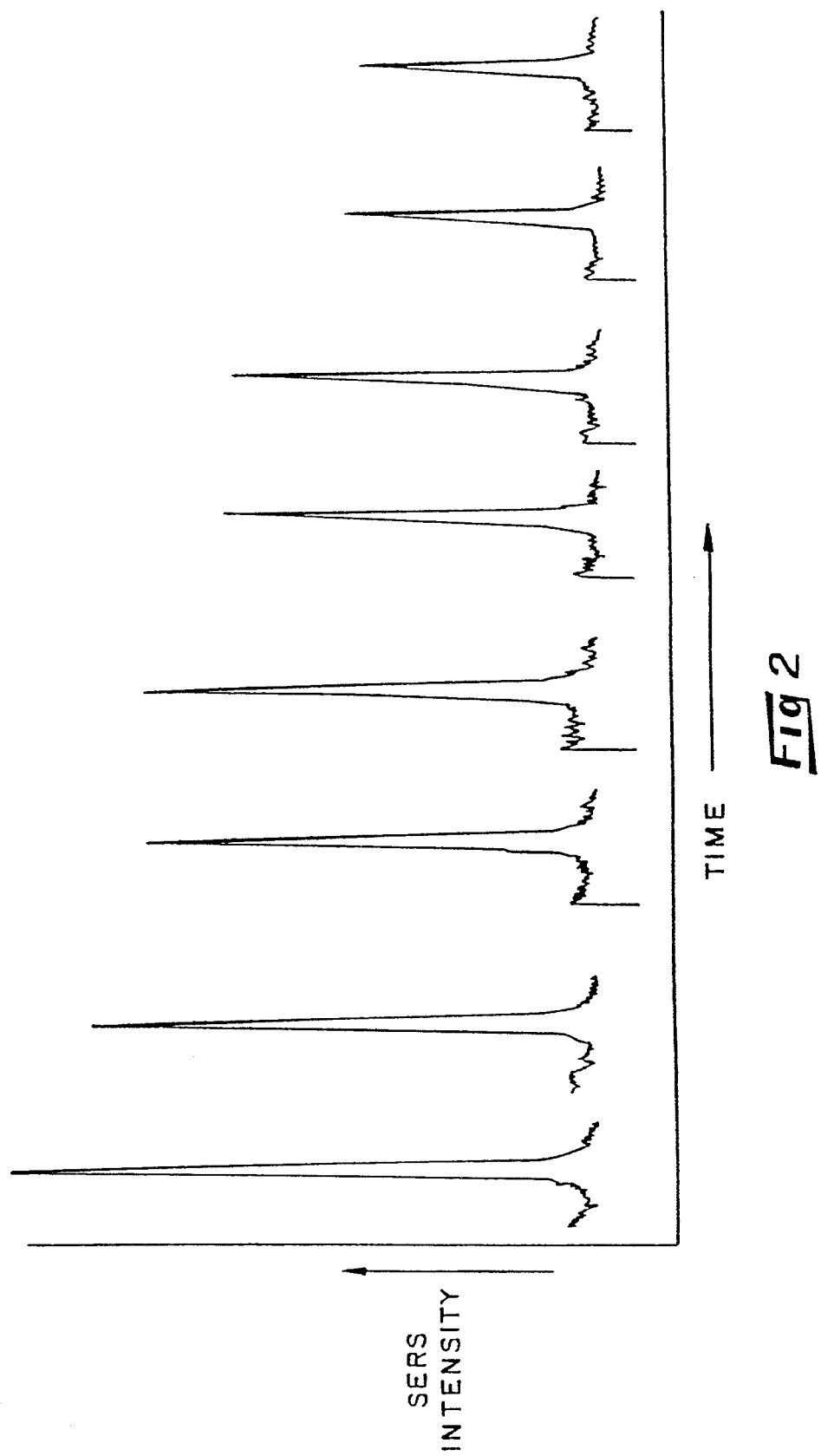
FIG. 2 is a graph showing the results of SERS-spectrometric analyses conducted on terephthalic acid.

FIG. 2 shows an example of the SERS signals of terephthalic acid (TPA) adsorbed on a collector made in accordance with Example 1. SERS measurements were accomplished by placing the collector into an aqueous solution of TPA (1 ppm) and then scanning the monochromator from 1500 cm$^{-1}$ to 1700 cm$^{-1}$ at an increment of 2 cm$^{-1}$ and an integration time of 4 seconds. The 647.1-nm line of a krypton ion laser was used for excitation, and the power was set at 200 mW. All measurements were conducted using either a fiber optic setup or a conventional Raman spectrometer. Monochromator slits were set at 800 $\mu$m.

Figure 3:
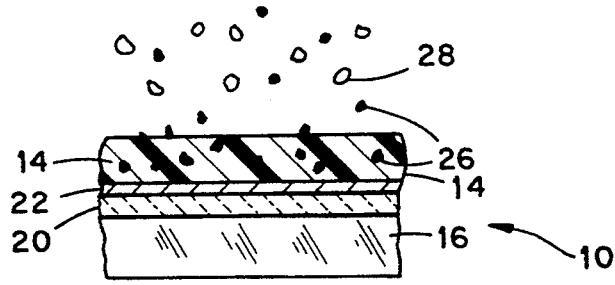
FIG. 3 is a cross-sectional end view of the collector of FIG. 1 showing specific chemicals adsorbed.

Referring now to FIG. 3, as noted, the coating 14 is selected based on its superior ability to absorb a specific chemical or biological compound 26. The coating sorbs the compound 26 and the compound 26 becomes positioned in the vicinity of the roughened surface 18 such that it exhibits the SERS effect and has a strong SERS signal when subsequently excited by a laser light such as used in conventional Raman signal readers. Non-sorbed compounds or species 28 remain outside the coating such that they do not experience a strong SERS effect. Thus, the collector of the present invention serves as both a sorbent agent and as a Raman inducer. In addition, the polymer coating 14 may be selected to sorb only specific chemicals (i.e. polar, nonpolar, ionic, and chemical specific groups), and bioreceptors (such as antibodies and enzymes) may be impregnated onto the coating to produce specific biosensors. Alternatively, a second, different metal layer may be used as a coating for some compounds; or the coating may be a semi-permeable membrane, specific pore site membrane, a membrane with a specific chemical affinity, or a membrane with ionic specificity may be utilized to alter the adsorption of the collector. A coating with improved nuclear radiation—hardening properties may also be used.

Example 2: Multiple Coatings

Figure 4:
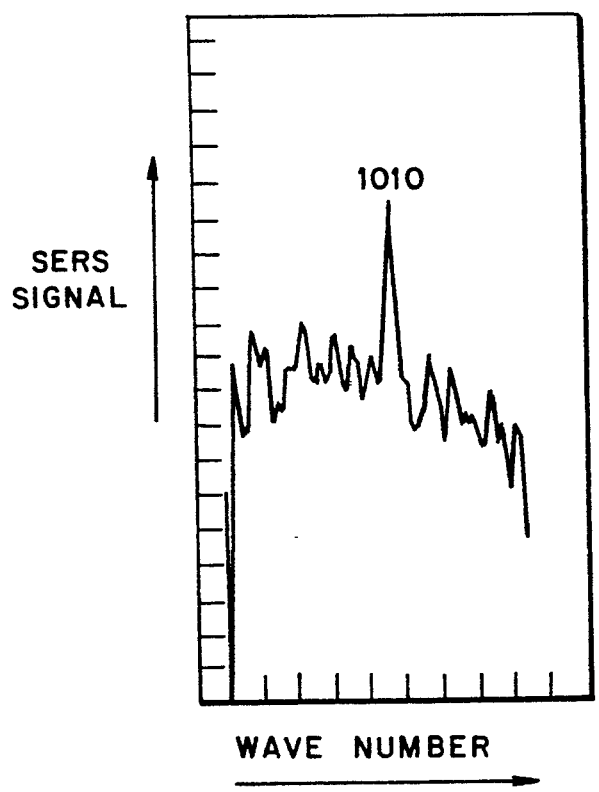
FIG. 4 is a graph showing the results of a SERS measurement conducted on benzoic acid adsorbed on a collector having a two-layer metal coating of gold and silver.

Several different metals or metal composites can also be used. FIG. 4 shows the SERS signal of benzoic acid (1.5 μg sample spot) adsorbed onto an alumina-based collector coated with a 75-nm layer of silver having a 1-nm overcoat of gold. The alumina-based substrate was prepared as in Example 1. The SERS measurement was accomplished using the 647.1-nm line of the krypton ion laser at 850-mW power.

Example 3: Antibody-Based Coating

Bioreceptors, such as antibodies or enzymes, can be used as coatings for SERS collectors. A SERS collector with microparticles of alumina coated with a layer of silver and a coating of polymer (prepared as described in Example 1) may be used. A method for coating consists of impregnating the polymer coating with a solution of known concentrations of bioreceptors. Following impregnation (e.g., 24 hours), the collectors are ready for use.

Figure 5:
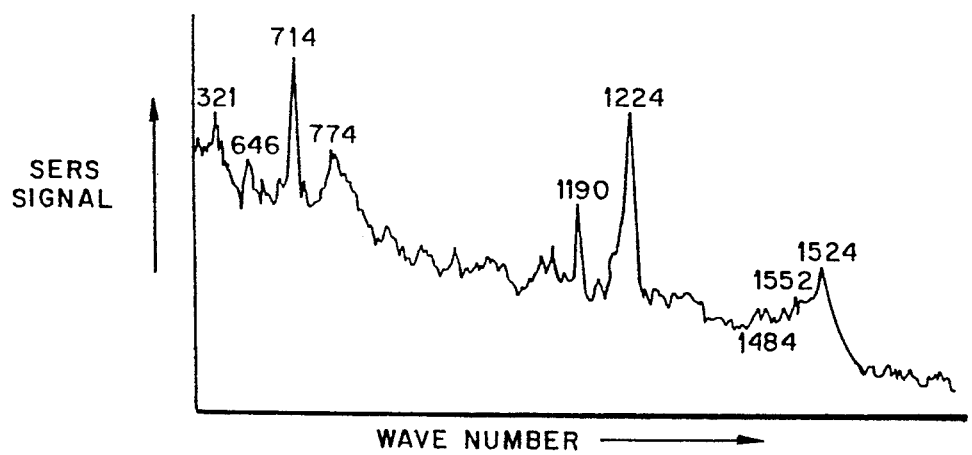
FIG. 5 is a graph showing the results of a SERS measurement conducted on ethenocytosine adsorbed on a SERS collector having an antibody-based coating.

An alternate method for coating with bioreceptors, such as antibodies, consists of delivering 5 mL of an antibody solution directly onto the alumina-based substrate coated with a silver layer. The substrates are then spun in a spinner at approximately 800 rpm for 20 sec. An optional protective overcoat (e.g., gel-based coating, nutrient based coating, agarose, etc.) may be used to protect, preserve or stabilize the bioreceptors. FIG. 5 shows an example of the SERS signal of 3-N ethenocytosine on a collector having an alumina-based substrate coated with a 100-nm layer of silver (prepared in accordance with Example 1), and having a coating of monoclonal antibodies against ethenocytidine. The antibody coating was prepared by spotting 5 mL of a diluted solution of antibody onto the SERS substrate and by spinning the substrate at 800 rpm for 20 sec. SERS measurements were accomplished by spotting 1 μL of a $10^{-3}$M solution of 3-N ethenocytosine onto the substrate and then scanning the monochromator from 200 to 1800 cm$^{-1}$. The 647.1-nm line of a krypton ion laser was used for excitation, and the power was set at 175 mW. The measurements demonstrate the use of antibody-coated collectors to detect SERS signals. The antibody against ethenocytidine is just one example. Other types of coatings having different antibodies against other chemicals, biological species, bacteria or viruses (e.g., AIDS, Herpes virus, etc.) may also be used.

Example 4: Enzyme

Another method for coating bioreceptors, such as enzymes, consists of binding the enzyme onto the SERS substrate surface. An example of an enzyme system is acetylcholinesterase (ACE). AcE is an enzyme that can hydrolyze a biochemical neurotransmitter called acetylcholine (Acy). The basic metabolism of Acy is interfered by certain types of compounds, such as pesticides, chemical nerve agents, and the like. These compounds (often referred to as "AcE Inhibitors" or AcI) bind to or near active sites of AcE and affect the action of AcE. One approach is to use a SER dosimeter/probe to detect the action of AcE in order to monitor the AcI compounds of interest. Another approach is to saturate all AcE (coated on a SERS collector) with a known AcI compound and monitor the displacement of the AcI by exposing the dosimeter/probe to a medium having unknown AcI chemicals (analytes) to be monitored. The SERS technique can be used to detect the competitive displacement of the known AcI by the analytes.

Figure 6:
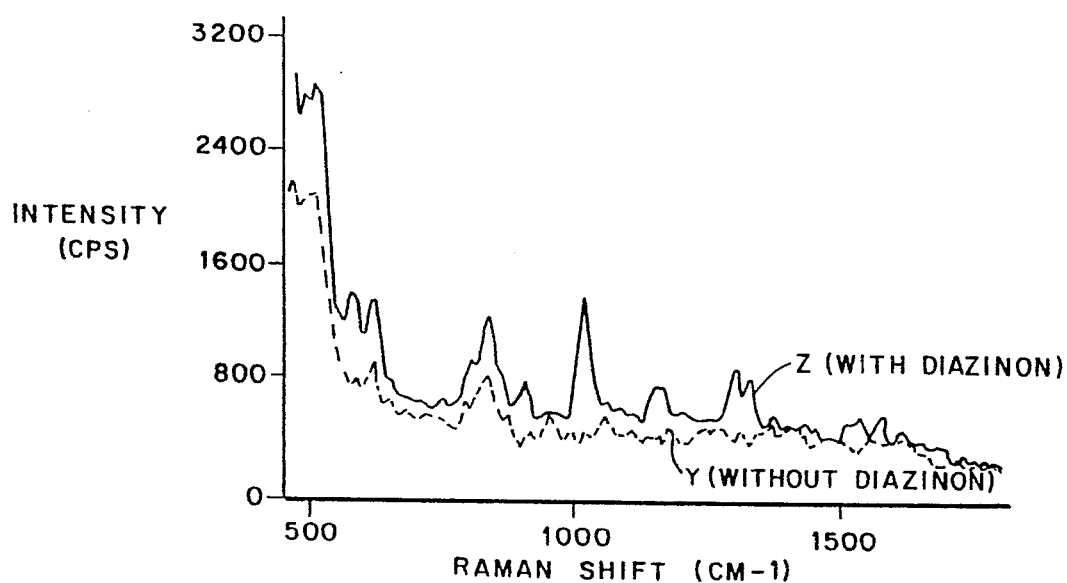
FIG. 6 is a graph showing the results of a SERS measurement conducted on diazinon adsorbed on a SERS collector having an enzyme-based coating.

FIG. 6 shows the results of SERS measurements of diazinon, a common pesticide, obtained with a SERS collector coated with AcE. SERS collectors were prepared with alumina and 100-nm layer of silver (see Example 1). AcE was attached to crosslinked Sepharose 6-B in order to stabilize the enzyme. Preparation of AcE-agarose was performed by incubation for 1 hr on ice using an equimolar solution of N-hydroxysuccinimide Sepharose 6-B (4% crosslinked, Siogma Chemical) with $4.5 \times 10^{-7}$M solution of AcE (Type, Sigma). After attaching AcE to the agarose, the reaction mixture was diluted to a final volume of 1.7 mL with distilled water. After boiling for 10 sec the solution was used for the preparation of AcE-agarose coatings. Coating with AcE-agarose was performed by spotting 20 μL of AcE-agarose onto the SERS collector and spinning the substrate at 6000 rpm for 20 sec. The analyte sample can be spotted onto the enzyme-based substrate. Alternatively, the collector may be exposed to a gas or liquid sample containing the analyte to be monitored. In FIG. 6, the difference in the SERS signals between curve Y (without diazinon) and curve Z (with diazinon) demonstrates the use of an enzyme-coated dosimeter/probe to detect AcI compounds such as diazinon. The measurements in FIG. 6 were accomplished by using the 647.1-nm line of a krypton ion laser at 50-mW power.

Figure 7:
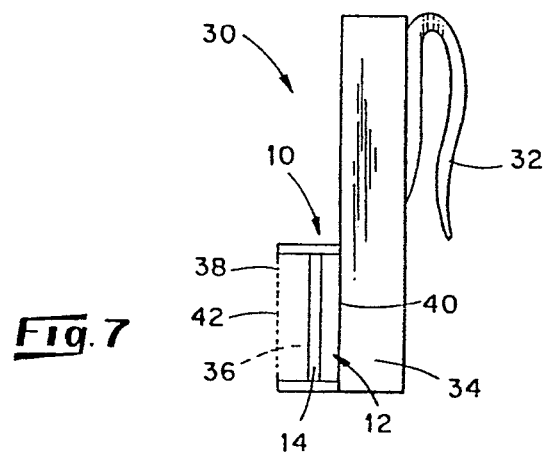
FIG. 7 is a cross-sectional side view of a dosimeter utilizing the collector of the present invention.

The collector 10 may be utilized in a dosimeter 30 (FIG. 7) which may be attached using a clip 32 to the clothing of personnel or may be placed at a stationary location. Referring further to FIG. 7, the dosimeter includes a base 34 attached to the clip 32 and a diffusion chamber 36 secured to and extending outward from the base to define an outer end 38 of the chamber 36 and an inner end 40 of the chamber positioned adjacent the base. The collector 10 is positioned within the chamber adjacent the inner end, and, optionally, a gas permeable membrane 42 may be secured within the outer end of the diffusion chamber to prevent unwanted chemical components from entering the chamber 36.

During sampling, the collector is exposed to the gas or liquid environment to be measured through the diffusion chamber 36. The coating 14 maintains the concentration of the sorbed chemicals at the surface of the collector at or near zero concentration while the environment outside the dosimeter is at ambient concentration. This provides a concentration gradient along the diffusion chamber for diffusion of the collected chemical or biological compounds from the outside of the dosimeter towards the roughened surface. This concentration gradient provides the driving force to position the monitored compounds in the vicinity of the roughened surface, eliminating the need for a pump.

The transfer of the monitored compounds by vapor diffusion is described by Fick's first law:

$$J = -D\frac{dc}{dl}$$

where
- D = coefficient of diffusion of the monitored compound ($cm^2$/sec)
- J = diffusion flux (moles/$cm^2$/sec)
- c = concentration (moles/$cm^3$)
- l = length of diffusion path (cm)

Figure 8:
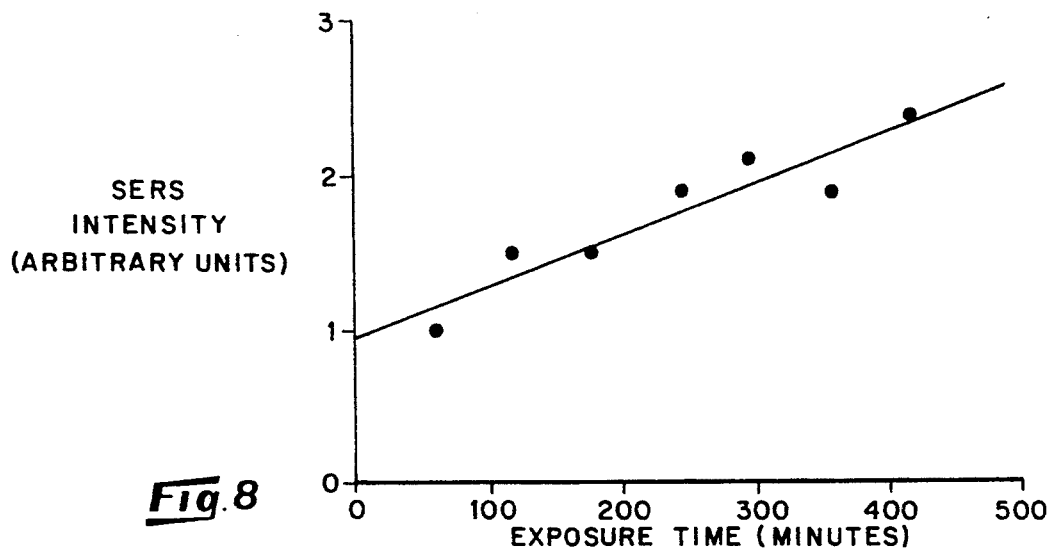
FIG. 8 shows the measurement of vapor of benzoic acid using the dosimeter of the present invention.

After a selected period of monitoring which may be predetermined or following an exposure to a chemical, the identity and level of the sorbed compounds are determined using conventional Raman signal reading techniques. FIG. 8 shows an example of measurement of benzoic acid vapor using the dosimeter described in this invention. The collector of the dosimeter is alumina covered with a 100-nm silver layer. The air-vapor concentration of benzoic acid is constant at 100 ppb (part-per billion). The laser line at 647.1 nm of a krypton ion laser was used for excitation.

Sequential Multiple Dosimeter/Probe

Figure 9:
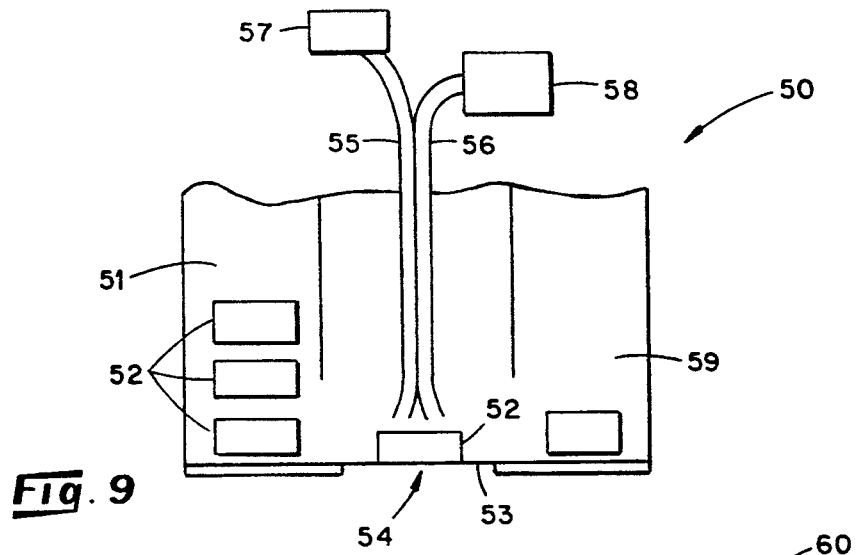
FIG. 9 is a schematic diagram of dosimeters used in an automated sequential multiprobes (ASM) device.

The collectors described above may be utilized in a automated sequential-multiprobe (ASM) 50 device shown schematically in FIG. 9. In this embodiment, a cartridge 51 (reservoir) contains a plurality of unexposed SERS probe/dosimeters 52 having appropriate coatings. A mechanical system 53, such as a conveyor driven by a stepping motor controlled by a microprocessor, may be utilized to sequentially position the SERS dosimeter/probes in a sampling area 54 for exposure to a sample (gas or liquid). When a probe is exposed to the sample, a SERS measurement is performed in conventional manner by way of optical fibers 55, 56 which are associated with a laser source 57 and a SERS emission database 58. After the measurement is completed, the exposed probe is retrieved by the mechanical system into a storage cartridge 59 and the next probe (unexposed) is positioned in the sampling area. The ASM device has several advantages: 1) automated and multiple measurements are possible, 2) a clean (unexposed) probe is available for each measurement, minimizing cross-contamination and avoiding the need for substrate cleaning. 3) after measurement, the probe can be stored for achieval purposes.

Dosimeter/Probe Array (DPA)

Figure 10:
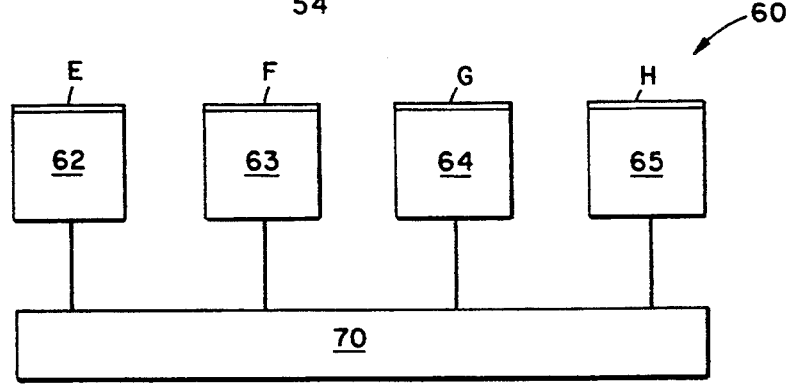
FIG. 10 is a schematic diagram of a multiple dosimeter/probe array.

Another embodiment of the present invention include an array 60 of SERS collectors 62, 63, 64, 65 coated with a number of different coatings E, F, G, H, respectively, as shown in FIG. 10. The SERS signal behavior and intensity of the array can be used for pattern recognition of individual chemicals. The array 60 is particularly useful to identify individual chemicals in a mixture. A parallel processor, shown generally at 70, is provided for analysis of SERS signals from the collectors. Analysis can be performed by a processor compatible with chemometric techniques, such as factor analysis, correlation method, Fourier transform technique, neural network analysis, and the like.

The foregoing description relates to certain embodiments of the present invention, and modifications or alterations may be made without departing from the spirit and scope of the invention as defined in the following claims.

What is claimed is:

1. A dosimeter and probe for qualitatively and quantitatively detecting predetermined materials in a gaseous environment to determine the presence of and exposure to predetermined such materials comprising:
   - a collector further comprising:
     - a SERS-active material; and
     - a coating applied to said SERS-active material having different sorptive properties for the predetermined materials than said SERS-active material, said coating being operable in the presence of the predetermined materials to sorb and thereby position the predetermined materials in the vicinity of said SERS-active material and thereby alter the SERS characteristics of said collector;
   - a dosimeter housing for isolating a volume from the environment, said volume containing said collector and isolating said collector from said environment; and
   - admission means for selectively admitting samples from the environment to said volume for exposure to said collector.

2. The collector of claim 1, wherein said surface-enhanced Raman spectroscopy-active material comprises:
   - a support surface; and
   - a roughened metallic layer adjacent said support surface.

3. The collector of claim 2, wherein said roughened metallic layer comprises:
   - a microstructure surface; and
   - a metal layer on said microstructure surface.

4. The collector of claim 1, wherein said coating comprises an organic polymer coating.

5. The collector of claim 1, wherein said coating comprises a polymethyl methacrylate coating.

6. The collector of claim 1, wherein said coating is selected from the group consisting of: Carnauba Wax, Ethyl cellulose, Ethylene maleic anhydride copolymer, Methyl vinyl ether, Octadecyl vinyl ether, Phenoxy resin, Poly 2-ethylhexyl methacrylate, Poly (Caprolactone), Poly (Caprolactone) triol, Poly-1-butadiene, Poly-n-butyl acrylate, Poly-p-vinyl phenol, Polybutadiene oxide, Polybutadiene hydroxy terminated, Polybutadiene-methylacrylated, Polycutadiene acrylonitrile, Polydecyl acetate, Polyethyl acrylate, Polyethylene, Polyethylene glycol methyl ether, Polyhexyl methacrylate, Poly 1 butene, Polymethacrylate, Polystyrene, Polyvinyl butyryl, Polyvinyl carbazole, Polyvinyl chloride, Polyvinyl isobutyl ether, Polyvinyl methyl ether, Polyvinyl stearate, and Vinyl alcohol/vinyl/acetate copolymer.

7. The collector of claim 1, wherein said coating comprises a multilayer metal coating at least two layers of metal.

8. The collector of claim 7, wherein the said multilayer coating comprises at least two layers of metal containing at least one metal chosen from the group consisting of gold and silver.

9. The collector of claim 1, wherein said coating comprises a nuclear radiation hardening material.

10. The collector of claim 1, wherein said coating comprises a carbon compound.

11. The collector of claim 1, further comprising a bioreceptor impregnated onto or attached onto said coating.

12. The collector of claim 11, wherein said bioreceptor comprises an antibody.

13. The collector of claim 11, wherein said bioreceptor comprises an enzyme.

14. A dosimeter for collection of a predetermined chemical or biological component for analysis by surface-enhanced Raman spectroscopy, said dosimeter comprising:
- a diffusion chamber secured to and extending outwardly from a base to define an outer end of said chamber and an inner end of said chamber adjacent to said base; and
- a collector positioned within said chamber, said collector comprising:
- a SERS-active material; and
- a coating applied to said SERS-active material having different sorptive properties for the predetermined component than said SERS-active material, said coating being operable in the presence of the predetermined component to sorb and thereby position the predetermined component in the vicinity of said SERS-active material and thereby alter the SERS characteristics of said collector.

15. The dosimeter of claim 14, wherein said predetermined component is present in a gas sample.

16. The dosimeter of claim 14, wherein said predetermined component is present in a liquid sample.

17. The dosimeter of claim 14, further comprising a gas permeable membrane positioned adjacent the outer end of said chamber to prevent unwanted chemical components from entering said chamber.

18. An automated sequential-multiprobe (ASM) device for monitoring predetermined materials, said ASM device comprising:
- a cartridge of unexposed collectors, each of said collectors comprising a SERS-active material, and a coating applied to said SERS-active material having different sorptive properties for the predetermined materials than said SERS-active material, said coating being operable in the presence of the predetermined materials to sorb and thereby position the predetermined materials in the vicinity of said SERS-active materials and thereby alter the SERS characteristics of said collectors;
- means for sequentially exposing each of said collectors to a sample medium; and
- means for retrieving said exposed collectors.

19. A dosimeter/probe array (DPA) device for monitoring predetermined materials, said DPA device comprising:
- a plurality of collectors, each of said collectors comprising a SERS-active material, and a coating applied to said SERS-active material having different sorptive properties for the predetermined materials than said SERS-active material, said coating being operable in the presence of the predetermined materials to sorb and thereby position the predetermined materials in the Vicinity of said SERS-active materials and thereby alter the SERS characteristics of said collectors; and
- means for analyzing the SERS signal of each one of said collectors which is exposed to an analyte.

* * * * *